(12) United States Patent
Hendrick et al.

(10) Patent No.: US 12,167,894 B2
(45) Date of Patent: Dec. 17, 2024

(54) CATHETER MOVEMENT CONTROL

(71) Applicant: THE SPECTRANETICS CORPORATION, Colorado Springs, CO (US)

(72) Inventors: Brandon Thomas Hendrick, Colorado Springs, CO (US); Blaine Andrew Schneider, Colorado Springs, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 692 days.

(21) Appl. No.: 16/245,086

(22) Filed: Jan. 10, 2019

(65) Prior Publication Data

US 2019/0142526 A1 May 16, 2019

Related U.S. Application Data

(63) Continuation of application No. 15/788,618, filed on Oct. 19, 2017, now Pat. No. 10,206,745, which is a
(Continued)

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/062* (2013.01); *A61B 5/064* (2013.01); *A61B 18/201* (2013.01);
(Continued)

(58) Field of Classification Search
CPC ....... A61B 34/20; A61B 18/201; A61B 90/98; A61B 5/062; A61B 5/064; A61B 18/20; A61B 2034/2051; A61B 2034/2055; A61B 2090/3954; A61B 2034/301; A61B 2017/00075; A61M 25/0116; A61M 25/0662; A61M 2205/502; A61M 25/0108; A61M 25/0113
See application file for complete search history.

(56) References Cited

U.S. PATENT DOCUMENTS 4,053,845 A 10/1977 Gould
4,641,912 A 2/1987 Goldenberg
(Continued)

FOREIGN PATENT DOCUMENTS

EP 0211984 B2 3/1987
EP 2319404 B1 5/2011
(Continued)

OTHER PUBLICATIONS

Abeysinghe et al. A Novel MEMS Pressure Sensor Fabricated On an Optical Fiber; IEEE Photonics Technology Letters vol. 13. No. 9 Sep. 2001 pp. 993-995.
(Continued)

*Primary Examiner* — Bo Joseph Peng

(57) ABSTRACT

An endovascular device monitoring system is provided that determines, based on movement of the endovascular device past a selected reference location, at least one of a movement rate of an endovascular device and position of a distal end of an endovascular device in a body of a patient.

20 Claims, 6 Drawing Sheets

Related U.S. Application Data continuation of application No. 15/488,911, filed on Apr. 17, 2017, now Pat. No. 9,827,055, which is a continuation of application No. 13/799,664, filed on Mar. 13, 2013, now Pat. No. 9,623,211.

(51) Int. Cl.

| | | |
|---|---|---|
| *A61B 18/20* | (2006.01) | |
| *A61B 90/98* | (2016.01) | |
| *A61M 25/01* | (2006.01) | |
| *A61M 25/06* | (2006.01) | |
| *A61B 17/00* | (2006.01) | |
| *A61B 34/30* | (2016.01) | |
| *A61B 90/00* | (2016.01) | |

(52) U.S. Cl.
 CPC ......... *A61B 90/98* (2016.02); *A61M 25/0116* (2013.01); *A61M 25/0662* (2013.01); *A61B 2017/00075* (2013.01); *A61B 18/20* (2013.01); *A61B 2034/2051* (2016.02); *A61B 2034/2055* (2016.02); *A61B 2034/301* (2016.02); *A61B 2090/3954* (2016.02); *A61M 25/0108* (2013.01); *A61M 25/0113* (2013.01); *A61M 2205/502* (2013.01)

(56) References Cited

U.S. PATENT DOCUMENTS

| | | |
|---|---|---|
| 4,669,465 A | 6/1987 | Moore et al. |
| 4,686,979 A | 8/1987 | Gruen et al. |
| 4,732,448 A | 3/1988 | Goldenberg |
| 4,747,405 A | 5/1988 | Leckrone |
| 4,769,005 A | 9/1988 | Ginsburg et al. |
| 4,784,132 A | 11/1988 | Fox et al. |
| 4,788,975 A | 12/1988 | Shturman et al. |
| 4,799,754 A | 1/1989 | Goldenberg |
| 4,807,620 A | 2/1989 | Strul et al. |
| 4,830,460 A | 5/1989 | Goldenberg |
| 4,844,062 A | 7/1989 | Wells |
| 4,848,336 A | 7/1989 | Fox et al. |
| 4,850,686 A | 7/1989 | Morimoto et al. |
| 4,913,142 A | 4/1990 | Kittrell et al. |
| 4,919,508 A | 4/1990 | Grace et al. |
| 4,924,863 A | 5/1990 | Sterzer |
| 4,925,265 A | 5/1990 | Rink et al. |
| 4,950,267 A * | 8/1990 | Ishihara ............... A61B 8/12 606/12 |
| 5,016,964 A | 5/1991 | Donnelly |
| 5,024,234 A | 6/1991 | Leary et al. |
| 5,026,366 A | 6/1991 | Leckrone |
| 5,029,588 A | 7/1991 | Yock et al. |
| 5,034,010 A | 7/1991 | Kittrell et al. |
| 5,040,548 A | 8/1991 | Yock |
| 5,041,108 A | 8/1991 | Fox et al. |
| 5,047,952 A | 9/1991 | Kramer et al. |
| 5,154,680 A | 10/1992 | Drzewiecki et al. |
| 5,165,897 A | 11/1992 | Johnson |
| 5,176,674 A | 1/1993 | Hofmann |
| 5,188,632 A | 2/1993 | Goldenberg |
| 5,207,672 A | 5/1993 | Roth et al. |
| 5,217,454 A | 6/1993 | Khoury |
| 5,243,546 A | 9/1993 | Maggard |
| 5,250,045 A | 10/1993 | Bohley |
| 5,263,953 A | 11/1993 | Bagby |
| 5,267,341 A | 11/1993 | Shearin |
| 5,300,085 A | 4/1994 | Yock |
| 5,304,171 A | 4/1994 | Gregory et al. |
| 5,318,032 A | 6/1994 | Lonsbury et al. |
| 5,350,375 A | 9/1994 | Deckelbaum et al. |
| 5,350,377 A | 9/1994 | Winston et al. |
| 5,350,395 A | 9/1994 | Yock |
| 5,352,197 A | 10/1994 | Hammersmark et al. |
| 5,377,683 A | 1/1995 | Barken |
| 5,395,361 A | 3/1995 | Fox et al. |
| 5,400,428 A | 3/1995 | Grace |
| 5,415,653 A | 5/1995 | Wardle et al. |
| 5,423,740 A | 6/1995 | Sullivan et al. |
| 5,425,355 A | 6/1995 | Kulick |
| 5,429,604 A | 7/1995 | Hammersmark et al. |
| 5,429,617 A | 7/1995 | Hammersmark et al. |
| 5,440,664 A | 8/1995 | Harrington et al. |
| 5,451,233 A | 9/1995 | Yock |
| 5,456,680 A | 10/1995 | Taylor et al. |
| 5,464,395 A | 11/1995 | Faxon et al. |
| 5,470,330 A | 11/1995 | Goldenberg et al. |
| 5,483,080 A | 1/1996 | Tam |
| 5,484,433 A | 1/1996 | Taylor et al. |
| 5,492,131 A * | 2/1996 | Galel ............... A61M 25/0105 600/114 |
| 5,514,128 A | 5/1996 | Hillsman et al. |
| 5,536,242 A | 7/1996 | Willard et al. |
| 5,571,151 A | 11/1996 | Gregory |
| 5,573,531 A | 11/1996 | Gregory |
| 5,623,940 A | 4/1997 | Daikuzono |
| 5,643,251 A | 7/1997 | Hillsman et al. |
| 5,649,923 A | 7/1997 | Gregory et al. |
| 5,657,760 A | 8/1997 | Ying et al. |
| 5,713,894 A | 2/1998 | Murphy-Chutorian et al. |
| 5,722,972 A | 3/1998 | Power et al. |
| 5,755,714 A | 5/1998 | Murphy-Chutorian |
| 5,792,118 A | 8/1998 | Kurth et al. |
| 5,800,350 A | 9/1998 | Coppleson et al. |
| 5,803,083 A | 9/1998 | Buck et al. |
| 5,807,377 A | 9/1998 | Madhani et al. |
| 5,817,144 A | 10/1998 | Gregory |
| 5,824,005 A | 10/1998 | Motamedi et al. |
| 5,824,026 A | 10/1998 | Diaz |
| 5,830,209 A | 11/1998 | Savage et al. |
| 5,836,946 A | 11/1998 | Diaz et al. |
| RE36,104 E | 2/1999 | Solar |
| 5,891,133 A | 4/1999 | Murphy-Chutorian |
| 5,938,602 A * | 8/1999 | Lloyd ............... A61B 8/4281 600/424 |
| 5,938,609 A | 8/1999 | Pomeranz |
| 5,976,124 A | 11/1999 | Reiser |
| 5,986,643 A | 11/1999 | Harvill et al. |
| 5,989,243 A | 11/1999 | Goldenberg |
| 6,022,342 A | 2/2000 | Mukherjee |
| 6,033,402 A | 3/2000 | Tu et al. |
| 6,036,715 A | 3/2000 | Yock |
| 6,056,743 A | 5/2000 | Ellis et al. |
| 6,066,130 A | 5/2000 | Gregory et al. |
| 6,117,128 A | 9/2000 | Gregory |
| 6,231,563 B1 | 5/2001 | White et al. |
| 6,251,104 B1 | 6/2001 | Kesten et al. |
| 6,287,297 B1 | 9/2001 | Woodruff et al. |
| 6,290,668 B1 | 9/2001 | Gregory et al. |
| 6,302,875 B1 | 10/2001 | Makower et al. |
| 6,370,411 B1 | 4/2002 | Osadchy et al. |
| 6,419,684 B1 | 7/2002 | Heisler et al. |
| 6,432,115 B1 | 8/2002 | Mollenauer et al. |
| 6,447,504 B1 | 9/2002 | Ben-Haim et al. |
| 6,447,525 B2 | 9/2002 | Follmer et al. |
| 6,458,098 B1 | 10/2002 | Kanesaka |
| 6,539,132 B2 | 3/2003 | Ivtsenkov et al. |
| 6,575,993 B1 | 6/2003 | Yock |
| 6,597,829 B2 | 7/2003 | Cormack |
| 6,733,495 B1 | 5/2004 | Bek et al. |
| 6,743,208 B1 | 6/2004 | Coyle |
| 6,792,390 B1 | 9/2004 | Burnside et al. |
| 7,238,178 B2 | 7/2007 | Maschke |
| 7,319,566 B2 | 1/2008 | Prince et al. |
| 7,568,619 B2 | 8/2009 | Todd et al. |
| 7,572,254 B2 | 8/2009 | Hebert et al. |
| 7,846,153 B2 | 12/2010 | Hebert et al. |
| 7,930,065 B2 | 4/2011 | Larkin et al. |
| 7,959,608 B2 | 6/2011 | Nash et al. |
| 7,988,633 B2 | 8/2011 | Hossack et al. |
| 8,016,745 B2 | 9/2011 | Hassler et al. |
| 8,016,748 B2 | 9/2011 | Mourlas et al. |
| 8,050,739 B2 | 11/2011 | Eck et al. |
| 8,100,893 B2 | 1/2012 | Dadisman |

(56) References Cited

U.S. PATENT DOCUMENTS

| | | |
|---|---|---|
| 8,361,097 B2 | 1/2013 | Patel et al. |
| 8,545,488 B2 | 10/2013 | Taylor et al. |
| 8,628,519 B2 | 1/2014 | Taylor et al. |
| 9,623,211 B2 | 4/2017 | Hendrick et al. |
| 9,827,055 B2 | 11/2017 | Hendrick et al. |
| 2001/0014805 A1 | 8/2001 | Burbank et al. |
| 2002/0013572 A1 | 1/2002 | Berlin |
| 2002/0026118 A1 | 2/2002 | Govari |
| 2002/0045811 A1 | 4/2002 | Kittrell et al. |
| 2002/0072661 A1 | 6/2002 | Wiesmann et al. |
| 2002/0103459 A1 | 8/2002 | Sparks et al. |
| 2002/0107445 A1 | 8/2002 | Govari |
| 2002/0159685 A1 | 10/2002 | Cormack |
| 2003/0032936 A1 | 2/2003 | Lederman |
| 2003/0045798 A1 | 3/2003 | Hular et al. |
| 2003/0078566 A1 | 4/2003 | Elliott et al. |
| 2003/0163040 A1* | 8/2003 | Gildenberg ............ A61B 34/20 600/429 |
| 2003/0204185 A1 | 10/2003 | Sherman et al. |
| 2003/0219202 A1 | 11/2003 | Loeb et al. |
| 2004/0010204 A1 | 1/2004 | Weber et al. |
| 2004/0059280 A1 | 3/2004 | Makower et al. |
| 2004/0075919 A1 | 4/2004 | Diaz et al. |
| 2004/0111016 A1 | 6/2004 | Casscells et al. |
| 2004/0127889 A1 | 7/2004 | Zhang et al. |
| 2004/0133154 A1 | 7/2004 | Flaherty et al. |
| 2004/0162548 A1 | 8/2004 | Reiser |
| 2005/0004453 A1 | 1/2005 | Tearney et al. |
| 2005/0033199 A1* | 2/2005 | van der Steen .......... A61B 8/12 600/587 |
| 2005/0096589 A1* | 5/2005 | Shachar ............ A61B 1/00158 604/95.01 |
| 2005/0149176 A1 | 7/2005 | Heggestuen et al. |
| 2005/0197566 A1* | 9/2005 | Strommer .......... A61B 1/00147 600/424 |
| 2005/0203416 A1 | 9/2005 | Angelsen et al. |
| 2005/0222518 A1* | 10/2005 | Dib ................... A61M 25/0067 600/562 |
| 2006/0020260 A1 | 1/2006 | Dover et al. |
| 2006/0094930 A1 | 5/2006 | Sparks et al. |
| 2006/0126788 A1* | 6/2006 | Engel .................... A61N 5/1001 378/119 |
| 2006/0217695 A1 | 9/2006 | DeBenedictis et al. |
| 2006/0247532 A1 | 11/2006 | Ramanujam et al. |
| 2007/0060879 A1 | 3/2007 | Weitzner et al. |
| 2007/0106289 A1 | 5/2007 | O'Sullivan |
| 2007/0115152 A1 | 5/2007 | Bjorklund et al. |
| 2007/0185377 A1* | 8/2007 | Murakami ....... A61B 17/32056 600/106 |
| 2007/0265610 A1* | 11/2007 | Thapliyal ........... A61B 18/1492 606/27 |
| 2008/0019657 A1 | 1/2008 | Maitland et al. |
| 2008/0058629 A1 | 3/2008 | Seibel et al. |
| 2008/0106388 A1 | 5/2008 | Knight |
| 2008/0108867 A1 | 5/2008 | Zhou |
| 2008/0154296 A1 | 6/2008 | Taylor et al. |
| 2009/0177095 A1 | 7/2009 | Aeby et al. |
| 2009/0203989 A1 | 8/2009 | Burnside et al. |
| 2009/0221958 A1* | 9/2009 | Beyar ..................... A61B 90/11 604/95.01 |
| 2010/0114081 A1 | 5/2010 | Keeler et al. |
| 2010/0152717 A1 | 6/2010 | Keeler |
| 2010/0168569 A1 | 7/2010 | Sliwa et al. |
| 2010/0177309 A1 | 7/2010 | Scaiano et al. |
| 2010/0200076 A1 | 8/2010 | Hieb et al. |
| 2011/0160681 A1 | 6/2011 | Dacey et al. |
| 2011/0196291 A1 | 8/2011 | Vischer et al. |
| 2011/0224649 A1 | 9/2011 | Duane et al. |
| 2011/0270091 A1 | 11/2011 | Hossack et al. |
| 2012/0181331 A1 | 7/2012 | Beden et al. |
| 2012/0253360 A1 | 10/2012 | White et al. |
| 2012/0302828 A1 | 11/2012 | Toledo-Crow et al. |
| 2013/0131579 A1 | 5/2013 | Mantell et al. |
| 2013/0253490 A1 | 9/2013 | Bitzer et al. |
| 2013/0338500 A1 | 12/2013 | Taylor et al. |
| 2014/0114298 A1 | 4/2014 | Taylor et al. |
| 2014/0276603 A1 | 9/2014 | Magee et al. |
| 2014/0276689 A1 | 9/2014 | Grace |
| 2014/0276690 A1 | 9/2014 | Grace |
| 2015/0011843 A1 | 1/2015 | Toth et al. |
| 2015/0141768 A1 | 5/2015 | Yu et al. |

FOREIGN PATENT DOCUMENTS

| | | |
|---|---|---|
| GB | 2208807 A | 4/1989 |
| WO | 1998019614 A1 | 5/1998 |
| WO | 2007115152 A2 | 10/2007 |
| WO | 2010042249 A4 | 8/2010 |

OTHER PUBLICATIONS

Advisory Action for U.S. Appl. No. 12/337,232 mailed Aug. 8, 2013, 3 pages.

Agency for Healthcare Research and Quality Adjunctive Devices in PCI To Remove Thrombi or Protect Against Distal Embolization in Patients With ACS: A Clinician Research Summary; Effective Health Care Program; AHRQ Pub. No. 11 (12)-EHC089-3 May 2012 4 pages.

Arifler et al. Light Scattering From Collagen Fiber Networks: Micro-Optical Properties of Normal and Neoplastic Stroma; Biophysical Journal vol. 92 May 2007, pp. 3260-3274.

Ashok et al. Raman Spectroscopy Sensor for Surgical Robotics—Instrumentation and Tissue Differentiation Algorithm Biomedical Optics and 3D Imaging OSA 2012 4 pages.

Bach et al., Design and Fabrication of 60-GB/s InP-Based Monolithic Photoreceiver OEICs and Modules, IEEE Journal of Selected Topics in Quantum Electronics, vol. 8, No. 6, Nov. 1, 2002, 6 pgs.

Baddour et al. Update On Cardiovascular Implantation Electronic Device Infections and Their Management: A Scientific Statement From the American Heart Association Circulation 121: Jan. 2010, pp. 458-477.

Badr et al. The State of the Excimer Laser for Coronary Intervention in the Drug-Eluting Stent Era Cardiovascular Revascularization Medicine 14, 2013, pp. 93-98.

Bann et al. Attitudes Towards Skills Examinations for Basic Surgical Trainees J. Clin Pract Jan. 2005, 59, 1. pp. 107-113.

Baztamica et al. Transvenous Extraction of Pacemaker Leads in Infective Endocarditis With Vegetations ≥ 20MM: Our Experience; Clinl. Cardiol 35, 4, 2012 pp. 244-249.

Beauvoit et al. Contribution of the Mitochondrial Compartment To the Optical Properties of the Rat Liver: A Theoretical and Practical Approach Biophysical Journal vol. 67 Dec. 1994 pp. 2501-2510.

Beccai et al. Design and Fabrication of a Hybrid Silicon Thre E-Axial Force Sensor for Biomechanical Applications; Sensors and Actuators A 120, 2005, pp. 370-382.

Berkelman et al. A Miniature Microsurgical Instrument Tip Force Sensor for Enhanced Force Feedback During Robotassisted Manipulation; IEEE Transactions on Robotics and Automaton, vol. 19, No. 5, Oct. 2003, pp. 917-922.

Bilodeau et al. Novel Use of a High-Energy Excimer Laser Catheter for Calcified and Complex Coronary Artery Lesions Catheterization and Cardiovascular Interventions 62: 2004 pp. 155-161.

Bindig et al. Fiber-Optical and Microscopic Detection of Malignant Tissue By Use of Infrared Spectrometry Journal of Biomedical Optics vol. 7 No. 1 Jan. 2002 pp. 100-108.

Bishop et al. Paid Malpractice Claims for Adverse Events in Inpatient and Outpatient Settings; JAMA vol. 205 No. 23 Jun. 15, 2011, pp. 2427-2431.

Bittl et al. Metaanalysis of Randomized Trials of Percutaneous Transluminal Coronary Angioplasty Versus Atherectomy, Cutting Balloon Atherotomy, or Laser Angioplasty Journal of the American College of Cardiology vol. 43 No. 6 2004 pp. 936-942.

Bongiorni et al. Transvenous Removal of Pacing and Implantable Cardiac Defibrillating Leads Using Single Sheath Mechanical Dilatation and Multiple Venous Approaches; High Success Rate and Safety in More Than 200 Leads; European Heart Journal vol. 29, 2008, pp. 2686-2893.

(56) References Cited

OTHER PUBLICATIONS

Bracke et al. Pacemaker Lead Complications: When is Extraction Appropriate and What Can We Learn From Published Data? Heart 2001 vol. 85 pp. 254-259.
Brennan et al. Analysis of Errors Reported By Surgeons At Three Teaching Hospitals, Surgery vol. 3, No. 6, 2003 pp. 614-621.
Britton Chance Optical Method; Annu Rev. Biophys. Chem vol. 20 1991 pp. 1-30.
Buch et al. Pacemaker and Defibrillator Lead Extraction; Circulation 2011:123 pp. 378-380.
Byrd et al. Clinical Study of the Laser Sheath for Lead Extraction: The Total Experience in the United States; Journal of Pacing and Clinical Electrophysiology, vol. 25 No. 5, May 2002 pp. 804-808.
Byrd et al. Intravascular Lead Extraction Using Locking Stylets and Sheaths; Pace vol. 13 Dec. 1990, pp. 1871-1875.
Candefjord et al. Combining Fibre Optic Raman Spectroscopy and Tactile Resonance Measurement for Tissue Characterization; Meas. Sci Technol. vol. 21, 2010 125801 8 pages.
Candinas et al. Postmortem Analysis of Encapsulation Around Long-Term Ventricular Endocardial Pacing Leads; Mayo Clin Proc. vol. 74, Feb. 1999, pp. 120-125.
Carlson et al. Motion Capture Measures Variability in Laryngoscopic Movement During Endotracheal Intubation: A Preliminary Report; 2012 Society for Simulation in Healthcare, vol. 7, No. 1, Aug. 2012 pp. 255-260.
Chan et al. Effects of Compression On Soft Tissue Optical Properties; IEEE Journal of Selected Topics in Quantum Electronics, vol. 2 No. 4, Dec. 1996 pp. 943-950.
Cheong et al. A Review of the Optical Properties of Biological Tissues; IEEE Journal of Quantum Electronics vol. 26, No. 12, Dec. 1990 pp. 2166-2185.
Chung et al. Advanced Fibre Bragg Grating and Microfibre Bragg Grating Fabrication Techniques; A Thesis Submitted in Partial Fulfillment of the Requirements for the Degree of Doctor of Philosophy The Hong Kong Polytechnic University; Mar. 2012; 130 pages.
Cruz et al. Internal Mammary Arterial Injury From Lead Extraction: A Clinically Subtle Yet Important Complication of Implantable Device Removal; Cardiology Research and Practice vol. 2011, Article ID 408640, (2011) 5 pages.
Da et al. Overview of the Vascular Interventional Robot; The International Journal of Medical Robotics and computer assisted surgery 2008;4: pp. 289-294.
Dallon et al. A Mathematical Model for Spatially Varying Extracellular Matrix Alighment; Siam J. Appl. Math. vol. 61, No. 2, 2000, pp. 506-527.
Deharo et al. Pathways for Training and Accreditation for Transvenous Lead Extraction: A European Heart Rhythm Association Position Paper; Europace 14 (2012) pp. 124-134.
Dipietro et al. Evaluaton of an Instrumented Glove for Hand-Movement Acquisition; Journal of Rehabilitation Research and Development vol. 40, No. 2, Mar./Apr. 2003, pp. 179-190.
Eichhorn et al. Carbon Nanotube Filled Composite Material Analysis Utilizing Nano and Conventional Testing Techniques; NIP & Digital Fabrication Conference, 2010 International Conference on Digital Printing Technologies. 5 Pages.
Eichhorn et al. Flexible Carbon Nanotube Composite Sensors for Medical Device Application; J. Med. Devices 7(2), 020943 (Jun. 11, 2013) (2 pages)Paper No. MED-13-1050; doi: 10.1115/1.4024311.
ELCA Coronary Laser Atherectomy Catheter Brochure, Spectranetics, 2012.
El-Sawah et al. A Prototype for 3-D Hand Tracking and Posture Estimation; IEEE Transactions on Instrumentation and Measurement, vol. 57, No. 8, Aug. 2008, pp. 1627-1636.
Endo et al. Clinical Utility of Intraprocedural Transesophagael Echocardiography During Transvenous Lead Extraction; Journal of the American Society of Echocardiography vol. 21 No. 7, Jul. 2008 pp. 862-867.

Epstein et al. Gross and Microscopic Pathological Changes Associated With Nonthoracotomy Implantable Defibrillator Lead; Circulation 1998:98: 1517-1524.
Erturk et al. Outcome of Surgery for Acromegaly Performed By Different Surgeons: Importance of Surgical Experience; Pituitary 8: 2005, pp. 93-97.
Esenaliev, O. R., et al. Laser Ablation of Atherosclerotic Blood Vessel Tissue Under Various Irradiation Conditions. IEEE Transactions on Biomedical Engineering, 36(12):1188-1194, Dec. 1989.
Esposito et al. Morphologic and Immunohistochemical Observations of Tissues Surrounding Retrieved Transvenous Pacemaker Leads; Wiley Periodicals, Inc. 2002, pp. 548-558.
European Search Report issued in EP Application No. 05796879.4 mailed Mar. 6, 2008, 7 pages.
European Search Report issued in EP Application No. 08010688.3. mailed Feb. 17, 2009, 6 pages.
Faber et al. Light Absorption of (Oxy–) Hemoglobin Assessed By Spectroscopic Optical Coherence Tomography; Optics Letters vol. 28, No. 16, Aug. 15, 2003 pp. 1436-1438.
Fanson et al. A System for Laparoscopic Surgery Ergonomics and Skills Evaluation; Journal of Endourology vol. 25, No. 7, Jul. 2011 pp. 1111-1114.
Final Official Action for U.S. Appl. No. 12/337,232 mailed Apr. 23, 2013, 11 pages.
Neuzil et al. Pacemaker and ICD Lead Extraction With Electrosurgical Dissection Sheaths and Standard Transvenous Extraction Systems: Results of a Randomized Trial; Europace 9, 2007, pp. 98-104.
Nikonovas et al. The Application of Force-Sensing Resistor Sensors for Measuring Forces Developed By the Human Hand; Proc. Insin Mech Engrs. vol. 218 Part H, 2004, 9 pages.
Nilsson et al Near Infrared Diffuse Reflection and Laser-Induced Fluorescence Spectroscopy for Myocardial Tissue Characterization; Spectrochimica ACTA Part A 53, 1997, pp. 1901-1912.
Noble et al. High Energy Excimer Laser To Treat Coronary in Stent Restenosis in an Under Expanded Stent; Catheter and Cardiovascular Interventions vol. 71, 2008, pp. 803-807.
Noonan et al. A Dual-Function Wheeled Probe for Tissue Viscoelastic Property Identification During Minimally Invasive Surgery; IEEE International Conference on Robotics and Automation, Apr. 10-14, 2007, 6 pages.
Notice of Allowance for U.S. Appl. No. 12/649,759 mailed May 16, 2013, 12 pages.
Notice of Allowance for U.S. Appl. No. 11/228,845 mailed Jun. 5, 2009, 8 pages.
Notice of Allowance for U.S. Appl. No. 12/406,807 mailed Aug. 2, 2010, 7 pages.
Notice of Alowance for U.S. Appl. No. 12/337,232 mailed Sep. 6, 2013, 11 pages.
Official Action for U.S. Appl. No. 11/228,845 mailed Jan. 12, 2009, 13 pages.
Official Action for U.S. Appl. No. 11/228,845 mailed Sep. 3, 2008, 10 pages.
Official Action for U.S. Appl. No. 12/337,232 mailed Mar. 23, 2012, 9 pages.
Official Action for U.S. Appl. No. 12/337,232 mailed Sep. 13, 2012, 10 pages.
Official Action for U.S. Appl. No. 12/649,759 mailed Aug. 30, 2012, 11 pages.
Official Action for U.S. Appl. No. 12/649,759 mailed Jul. 16, 2012, 9 pages.
Okumura et al. A Systematic Analysis of in Vivo Contact Forces On Virtual Catheter Tip/Tissue Surface Contact During Cardiac Mapping and Intervention; J. Cardiovasc Bectrophysiol, vol. 19, Jun. 2008, pp. 632-640.
Orengo et al. Characterization of Piezoresistive Sensors for Goniometric Glove in Hand Prostheses; Wireless VITAE, 2009 pp. 684-687.
Park et al. Exoskeletal Force-Sensing End-Effectors With Embedded Optical Fiber-Bragg Grating Sensors; IEEE Transactions on Robotics, vol. 25, No. 6, Dec. 2009, pp. 1319-1331.
Park et al. Fingertip Force Control With Embedded Fiber Bragg Grating Sensors; IEEE conference on Robotics and Automation, May 19-23, 2008, pp. 3431-3436.

(56) References Cited

OTHER PUBLICATIONS

Park et al. Force Sensing Robot Fingers Using Embedded Fiber Bragg Grating Sensors and Shape Deposition Manufacturing;; IEEE International Conference on Robotics and Automation, Apr. 10-14, 2007,. pp. 1510-1516.
Parker et al. Advanced Imaging Catheter Gives Surgeons the Inside Picture; Brochure Jun. 12, 2013: https//www.linl.gov/str/DaSilva. html.
Patterson et al. Time Resolved Reflectance and Transmittance for the Non-Invasive Measurement of Tissue Optical Properties; Applied Optics vol. 28, No. 12, Jun. 15, 1989 pp. 2331-2336.
Peracchia Surgical Education in the Third Millennium; Annuals of Surgery, vol. 234, No. 6. 2001. pp. 709-712.
Pettit et al. Dynamic Optical Properties of Collagen-Based Tissue During ARF Excimer Laser Ablation; Applied Optics vol. 32, No. 4 Feb. 1, 1993, pp. 488-493.
Piers et al. A Micro Optical Force Sensor for Force Feedback During Minimally Invasive Robotic Surgery; Elsevier Sensors and Actuators A 115, 2004, pp. 447-455.
Polygerinos et al. MRI-Compatible Fiber-Optic Force Sensors for Catheterization Procedures; IEEE Sensors Journal vol. 10 No. 10, Oct. 2010, pp. 1598-1608.
Post et al.; Outcome After Complete Percutaneous Removal of Infected Pacemaker Systems and Implantable Cardiac Defibrillators; Internal Medicine Journal 36, 2006, pp. 790-792.
Prasad et al. A Modular 2-DOF Force-Sensing Instrument for Laparoscopic Surgery; MICCAI 2003, LNCS 2878 pp. 279-286.
Puangmali et al. State-of-the Art in Force and Tactile Sensing for Minimally Invasive Surgery; IEEE Sensors Journal vol. 8, No. 4, Apr. 2008, pp. 371-381.
Rajan et al. Photonic Crystal Fiber Sensors for Minimally Invasive Surgical Devices; IEEE Transactions on Biomedical Engineering, vol. 59, No. 2, Feb. 2012, pp. 332-338.
Reiley et al. Review of Methods for Objective Surgical Skill Evaluation Surg Endosc, vol. 25, 2011 pp. 356-366.
Richards et al. Skills Evaluation in Minimally Invasive Surgery Using Force/Torque Signatures Surg Endosc vol. 14, 2000, pp. 791-798.
Rinaldi et al. Determinants of Procedural Outcome of Chronically Implanted Pacemaker and Defibrillator Leads Using the Excimer Laser Sheath Heart.bmj.com, Dec. 5, 2012, 3 pages.
Rocha et al. Fluorescence and Reflectance Spectroscopy for Identification of Atherosclerosis in Human Carotid Arteries Using Principal Components Analysis; Photomedicine and Laser Surgery vol. 26, No. 4, 2008, pp. 329-335.
Rosen et al. Markov Modeling of Minimally Invasive Surgery Based on Tool/Tissue Interaction and Force/Torque Signatures for Evaluating Surgical Skills; IEEE Transactions on Biomedical Engineering, vol. 48, No. 5 May 2001, 13 pages.
Rovithakis Artificial Neural Networks for Discriminating Pathologic From Normal Peripheral Vascular Tissue; IEEE Transactions on Biomedical Engineering, vol. 48, No. 10, Oct. 2001 pp. 1088-1097.
Ruttmann et al. Transvenous Pacemaker Lead Removal is Safe and Effective Even in Large Vegetations: An Analysis of 53 Cases of Pacemaker Lead Endocarditis; Pace vol. 26, Mar. 2006 pp. 231-236.
Sangpradit et al. Tissue Identification Using Inverse Finite Element Analysis of Rolling Indentation: 2009 IEEE International Conference on Robotics and Automation; Kobe, Japan, May 12, 17, 2009, 6 pages.
Schroeder et al. Visualizing Surgical Training Databases: Exploratory Visualization, Data Modeling, and Formative Feedback for Improving Skill Acquisition: IEEE Computer Graphics and Applications, 2011, 11 pages; DOI 10.1109/MCG.2012.67.
Seibold et al. Prototype of Instrument for Minimally Invasive Surgery With 6-Axis Force Sensing Capability; Proceedings of the 2005 IEEE International Conference on Robotics and Automation, Apr. 2005, 6 pages.
Sensor-Response-Compressive Force versus CNT sensor readout Chart, 2 pages.
Shah et al. Evaluation of a New Catheter Sensor for Real-Time Measurement of Tissue Contact; Heart Rhythm, vol. 3, No. 5, Supplement, May 2006 pp. S75-S76.
Simone et al. A Low Cost Instrumented Glove for Extended Monitoring and Functional Hand Assessment; Journal of Neuroscience Methods 160, 2007 pp. 335-348.
Smith et al. Extraction of Transvenous Pacing and ICD Leads; Pace vol. 31 Jun. 2008 pp. 736-752.
Sohail et al. Management and Outcome of Permanent Pacemaker and Implantable Cardioverter-Defibrillator Infections; Journal of the American College of Cardiology, vol. 49, No. 18, 2007 pp. 1851-1859.
Sokollik et al. New Model for Skills Assessment and Training Progress in Minimally Invasive Surgery; Surg Endosc vol. 18, 2004, pp. 495-500.
Sosa et al. The Importance of Surgeon Experience for Clinical and Economic Outcomes From Thyroidectomy; Annals of Surgery vol. 226, No. 3 pp. 320-330, Sep. 1998.
Spectranetics User Manual VisiSheath Dilator Sheath, 2011, 112 pages.
Spectranetics X80 User Manual ELCA Coronary Laser Atherectomy Catheter. Mar. 2012, 16 pages.
Spectranetics. ELCA Coronary Laser Atherectomy Catheter: Instructions for Use, 0.9 mm OTW and 0.9 mm RX X-80 Catheter Models, Mar. 14, 2012, pp. 1-16.
SPI2006 Shear Sensor Brochure—Real-Time Surface Shear Sensing Application: Human Interface; Tactilus Technology, 2006, 1 page.
Sturman et al. A Survey of Glove-Based Input; Clumsy Intermediary Devices Constrain Our Interaction With Computers and Their Applications. Glove-Based Input Devices Let Us Apply Our Manual Dexterity To the Task: IEEE Computer Graphics & Applications, Jan. 1994. pp. 30-39.
Sun et al. A Sub-Millemetric, 0.25 Mn Resolution Fully Integrated Fiber-Optic Force Sensing Tool for Retinal Microsurgery; Int J Comput Assist Radiol Surg. vol. 4(4): Jun. 2009, pp. 383-390.
Takano et al. Changes in Coronary Plaque Color and Morphology By Lipid-Lowering Therapy With Atorvastatin: Serial Evaluation By Coronary Angioscopy; The Journal of the American College of Cardiology, vol. 42, No. 4, 2003 pp. 680-686.
Taroni et al. In Vivo Absorption and Scattering Spectroscopy of Biological Tissues; Photochem. Photobiol. Sci. vol. 2, 2003. pp. 124-129.
Turchin et al. Novel Algorithm of Processing Optical Coherence Tomography Images for Differentiation of Biological Tissue Pathologies; Journal of Biomedical Optics 10(6), Nov./Dec. 2005, 11 pages.
Turner et al. Development and Testing of a Telemanipulation System With Arm and Hand Motion; Accepted to 2000 ASME IMECE Symp. Haptic Interfaces, 2000, 7 pages.
U.S. Appl. No. 14/586,312, filed Dec. 30, 2014.
U.S. Appl. No. 14/586,529, filed Dec. 30, 2014.
U.S. Appl. No. 14/586,543, filed Dec. 30, 2014.
Valdastri et al. Integration of a Miniaturized Triaxial Force Sensor in a Minimally Invasive Surgical Tool; IEEE Transactions on Biomedical Engineering, vol. 53, No. 11, Nov. 2006 pp. 2397-2400.
Van der Meer et al. Quantitative Optical Coherence Tomography of Arterial Wall Components; Lasers in Medical Science vol. 20, 2005, pp. 45-51.
Van der Meijden et al. The Valve of Haptic Feedback in Conventional and Robo T-Assisted Minimal Invasive Surgery and Virtual Reality Training: A Current Review; Surg. Endosc vol. 23, 2009. pp. 180-1190.
Van Leeuwen et al. Origin of Arterial Wall Dissections Induced By Pulsed Excimer and Mid-Infrared Laser Ablation in the PIGL; JACC vol. 19, No. 7, Jun. 1992, pp. 1610-1618.
Van Lindert et al. The Influence of Surgical Experience On the Rate of Intraoperative Aneurysm Rupture and Its Impact On Aneurysm Treatment Outcome; Surg Neurol vol. 56, 2001, pp. 151-158.
Wagner et al. The Role of Force Feedback in Surgery: Analysis of Blunt Dissection; Presented at the Tenth Symposium on Haptic Interfaces for Virtual Environment and Teleoperator Systems, Mar. 24, 25, 2002, 7 pages.

(56) References Cited

OTHER PUBLICATIONS

Walker et al. Surgical Safety Checklists: Do They Improve Outcomes?; British Journal of Anaesthesia, 2012, pp. 1-8.
Wang et al. Characterization of a Silicon=Based Shear-Force Sensor On Human Subjects; IEEE Trans Biomed Eng., 2002 1 page.
Wang et al. Miniature All-Silica Optical Fiber Pressure Sensor With an Ultrathin Uniform Diaphragm; Optics Express vol. 18, No. 9, Apr. 26, 2010 pp. 9006-9014.
Wang et al. Review: The Physiological and Computational Approaches for Atherosclerosis Treatment; IJCA-15372, 2012, 13 pages.
Wang, Lin et al. "Characterization of a Silicon-Based Shear-Force Sensor on Human Subjects." IEEE Transactions on Biomedical Engineering, vol. 49, No. 11. Nov. 2002. pp. 1340-1347.
Wazni et al. Lead Extraction in the Contemporary Setting: The Lexicon Study; Journal of the American College of Cardiology vol. 55, No. 6, 2010, pp. 579-586.
Weiss et al. Muscular and Postural Synergies of the Human Hand; J. Neurophysiol 92, 2004 pp. 523-535.
Wikipedia, Linear discriminant analysis, Dec. 21, 2013, http://en.wikipedia.org/wiki/Linear_discriminant_analysis.
Wilkoff et al. Transvenous Lead Extraction: Heart Rhythm Society Expert Consensus On Facilities, Training, Indications, and Patient Management; Heart Rhythm, vol. 6, No. 7, Jul. 2009, pp. 1086-1104.
Wise et al. Evaluation of a Fiber Optic Glove for Semi-Automated Goniometric Measurements; Journal of Rehabilitation Research and Development vol. 27 No. 4, 1990, pp. 411-424.
Wollmann et al. Two Different Therapeutic Strategies in ICD Lead Defects: Additional Combined Lead Versus Replacement of the Lead; Journal of Cardiovascular Electrophysiology vol. 18, No. 11. Nov. 2007, pp. 1172-1177.
Yamamoto et al. Tissue Property Estimation and Graphical Display for Teleoperated Robot-Assisted Surgery; 2009 IEEE International Conference on Robotics and Automation, May 12, 17, 2009, 7 pages.
Yokoyama et al. Novel Contact Force Sensor Incorporated in Irrigated Radiofrequency Ablation Catheter Predicts Lesion Size and Incidence of Steam Pop and Thrombus Clinical Perspective; Circulation Arrhythmia and electrophysiology: Journal of the American Heart Association, Dec. 2008, pp. 353-362.
Yun et al. An Instrumented Glove for Grasp Specification in Virtual-Reality-Based Point and Direct Telerobotics; IEEE Transactions on Systems, Man, and Cybernetics—Bart B: Cybernetics, vol. 27, No. 5, Oct. 1997, pp. 835-846.
Zhan et al. Excess Length of Stay, Charges, and Mortality Attributable To Medical Injuries During Hospitalization; Journal of American Medical Association, vol. 290, No. 14, Oct. 8, 2003, pp. 1868-1874.
U.S. Appl. No. 15/488,911, filed Apr. 17, 2017.
U.S. Appl. No. 13/799,664, filed Mar. 13, 2013.
Fung et al. A PMMA Based Micro Pressure Sensor Chip Using Carbon Nanotubes as Sensing Elements; IEEE International Conference On Micro Electro Mechanical Systems, vol. 18, 2005 pp. 251-254.
Ghosh et al. Laser Lead Extraction: Is There a Learning Curve?; Pace, vol. 28; Mar. 2005 pp. 1180-1184.
Golzio et al. Prevention and Treatment of Lead Extraction Complications; Transvenous Lead Extraction; Springer-Verlag Italia 2011 pp. 129-136.
Griffin et al. Calibration and Mapping of a Human Hand for Dexterous Telemanipulation; ASME IMECE Conference, 2000, 8 pages.
Grundfest, Warren S., MD, et al., "Laser Ablation Of Human Atherosclerotic Plaque Without Adjacent Tissue Injury," JACC vol. 5, No. 4, (Apr. 1985), pp. 929-933.
Hager Ross et al. Quantifying the Independence of Human Finger Movements: Comparisons of Digits, Hands, and Movement Frequencies; The Journal of Neurosciences, vol. 20 No. 22, Nov. 15, 2000, pp. 8542-8550.
Hajarian et al. Intravascular Laser Speckle Imaging Catheter for the Mechanical Evaluation of the Arterial Wall; Journal of Biomedical Optics vol. 16(2) Feb. 2011, 7 pages.
Hanke et al. Morphological Changes and Smooth Muscle Cell Proliferation After Experimental Excimer Laser Treatment; Circulation vol. 83, 1991 pp. 1380-1389.
Hattori et al. Invivo Raman Study of the Living Rat Esophagus and Stomach Using a Micro-Raman Probe Under an Endoscope; Applied Spectroscopy vol. 61, No. 6, 2007, 8 pages.
Hauser Deaths and Cardiovascular Injuries Due To Device-Assisted Implantable Cardioverter-Defibrillator and Pacemaker Lead Extraction; Europace vol. 12, 2010, pp. 395-401.
Henning et al. An In Vivo Strain Gage Study of Elongation of the Anterior Cruciate Ligament; The American Journal of Sports Medicine, vol. 13, No. 1m 1985, pp. 22-26.
Inmann et al. An Instrument Object for Evaluation of Lateral Hand Grasp During Functional Tasks; Journal of Medical Engineering & Technology, vol. 25. No. 5, Sep./Oct. 2001, pp. 207-211.
Insull The Pathology of Atherosclerosis; Plaque Development and Plaque Responses To Medical Treatment; The American Journal of Medicine, vol. 122, No. 1A, Jan. 2009, 12 pages.
Interlink Electronics. State-of-the-Art Pointing Solutions for the OEM—FSR Force Sensing Resistor Integration Guide and Evaluation Parts Catalog: 400 Series Evaluation Parts With Suggested Electrical Interfaces. Interlink Electronics, Version 1.0 (90-45632 Rev. D), Camarillo, CA, pp. 1-26.
International Preliminary Report on Patentability issued in PCT/US2009/066133, mailed Jun. 21, 2011, 8 pages.
International Search Report and Written Opinion Issued in PCT/2014/019258, mailed Aug. 8, 2014, 21 pages.
International Search Report and Written Opinion issued in PCT/2014/019283, mailed Jun. 20, 2014, 15 pages.
International Search Report and Written Opinion issued in PCT/2014019278, mailed May 7, 2014, 14 pages.
International Search Report and Written Opinion issued in PCT/US2005/033029, mailed Oct. 3, 2006, 1 page.
International Search Report and Written Opinion issued in PCT/US2009/066133, mailed Jan. 26, 2010, 8 pages.
Jagsi et al. Original Investigation: Residents Report On Adverse Events and Their Causes; Arch Intern Med/ vol. 163 Dec. 12/26, 2005 7 pages.
Johns et al. Determination of Reduced Scattering Coefficient of Biological Tissue From a Needle-Like Probe; Optics Express vol. 13, No. 13. Jun. 27, 2005 pp. 4828-4842.
Kahol, K. et al. Effect of Fatigue on Psychomotor and Cognitive Skills. The American Journal of Surgery: Association for Surgical Education, 195:195-204, 2008.
Kane et al. A Traction Stress Sensor Array for Use in High-Resolution Robotic Tactile Imaging; Journal of Microelectromechanical Systems, vol. 9, No. 4, Dec. 2000, pp. 425-434.
Kang et al. A Carbon Nanotube Strain Sensor for Structural Health Monitoring; Smart Matter. Struct. vol. 15, 2006, pp. 737-748.
Karimov et al. A Carbon Nanotube-Based Pressure Sensor, Phys. Scr. 83, 2011, 5 pages.
Karsch et al. Percutaneous Coronary Excimer Laser Angioplasty Initial Clinical Results; The Lancet, Sep. 16, 1989 pp. 647-650.
Kennergren Excimer Laser Assisted Extraction of Permanent Pacemaker and ICD Leads: Present Experiences of a European Multi-Centre Study; European Journal of Cardio Thoracic Surgery 15, 1990, pp. 856-860.
Khairy et al. Laser Lead Extraction in Adult Congenital Heart Disease; J. Cardiovasc Electrophysiol, vol. 16, 2006, pp. 507-511.
Khalil et al. Tissue Elasticity Estimation With Optical Coherence Elastography: Toward Mechanical Characterization of In Vivo Soft Tissue; Annals of Biomedical Engineering, vol. 33, No. 11, Nov. 2005, pp. 1631-1639.
Kochiadakis et al. The Role of Laser-Induced Fluorescence in Myocardial Tissue Characterization: An Experimental Invitro Study; Chest vol. 120, 2001, pp. 233-239.
Koulouris et al. Intravascular Lead Extractions: Tips and Tricks; Intech Open Science/Open Minds http//creativecommons.org/licenses/by/3.0, 2012 pp. 189-216.

(56) References Cited

OTHER PUBLICATIONS

Kremers et al. The National ICD Registry Report: Version 2.1 Including Leads and Pediatrics for Years 2010 and 2011; pp. 59-65.
Lathan et al. The Effects of Operator Spatial Perception and Sensory Feedback On Human-Robot Teleoperation Performance; Presence, vol. 11, No. 4, Aug. 2002, 368-377.
Levine et al. 2011 ACCF/AHA/SCAI Guideline for Percutaneous Coronary Intervention: Executive Summary; Journal of the American College of Cardiology vol. 58, No. 24, 2011, pp. 2250-2583.
Li et al. Strain and Pressure Sensing Using Single-Walled Carbon Nanotubes; Nanotechnology vol. 15, 2004, pp. 1493-1498.
Lieber et al. Sarcomere Length Determination Using Laser Diffraction: Effect of Beam and Fiber Diameter; Biophys J. vol. 45, May 1984, pp. 1007-1016.
Lipomi et al. Skin-Like Pressure and Strain Sensors Based on Transparent Elastic Films of Carbon Nanotubes; Nature Nanotechnology, vol. 6, Dec. 2011, pp. 788-792.
Maréchal, L. et al. "Measurement System for Gesture Characterization During Chest Physiotherapy Act on Newborn Babies Suffering from Bronchiolitis." Proceedings of the 29th Annual International Conference of the IEEE Embs, Cité Internationale, Lyon, France. Aug. 23-26, 2007. pp. 5770-5773.
Maytin et al. Multicenter Experience With Extraction of the Sprint Fidelis Implantable Cardioverter-Defibrillator Lead; Journal of the American College of Cardiology vol. 56, No. 8, 2010, pp. 642-646.
Maytin et al. The Challenges of Transvenous Lead Extraction; Heart vol. 97, 2011, pp. 425-434.
Medtronic's Brochure; Implantable Pacemaker and Defibrillator Information; Apr. 2006, 2 pages.
Meier-Ewert et al. Endocardial Pacemaker or Defibrillator Leads With Infected Vegetations: A Single-Center Experience and Consequences of Transvenous Extraction; Am Heart Journal vol. 146, 2003, pp. 339-344/.
Menciassi et al. Force Sensing Microinstrument for Measuring Tissue Properties and Pulse in Microsurgery, IEEE/ASME Transactions on Mechatronics, vol. 8, No. 1, Mar. 2003, pp. 10-17.
Mishra et al. Fiber Grating Sensors in Medicine: Current and Emerging Applications; Sensors and Actualtors A, 167, 2011, pp. 279-290.
Missinne Flexible Miniature Shear Sensors for Prosthetics; SPIE Newsroom SPIE, May 13, 2013, 4 pages.
Missinne, Jeroen et al. "Embedded Flexible Optical Shear Sensor." IEEE Sensors 2010 Conference. 2010. pp. 987-990.
Mond et al. The Electrode-Tissue Interface: The Revolutionary Role of Steroid Elution; Pace vol. 15, Jan. 1992, pp. 95-107.
Moscato et al. A Micromachined Intensity-Modulated Fiber Optic Sensor for Strain Measurements: Working Principle and Static Calibration; 34th Annual International Conference of the IEEE EMBS, 2012, pp. 5790-5793.
Mujat et al.; Automated Algorithm for Breast Tissue Differentiation in Optical Coherence Tomogrpahy; Journal of Biomedical Optics 14(3), 2009, 9 pages.

\* cited by examiner

CATHETER MOVEMENT CONTROL

CROSS REFERENCE TO RELATED APPLICATION

The present application is a continuation of U.S. patent application Ser. No. 15/788,618, filed Oct. 19, 2017, which is a continuation of U.S. application Ser. No. 15/488,911, filed on Apr. 17, 2017, issued as U.S. Pat. No. 9,827,055 on Nov. 28, 2017, which is a continuation of U.S. application Ser. No. 13/799,664, filed on Mar. 13, 2013, issued as U.S. Pat. No. 9,623,211 on Apr. 18, 2017, all of which are hereby incorporated herein by reference in all their entirety for all that they teach and for all purposes.

FIELD

The disclosure relates generally to endovascular devices and particularly to monitoring the use of catheters.

BACKGROUND

Catheters are medical devices that can be inserted into a body cavity, duct, or vessel to treat diseases or perform a surgical procedure. Catheterization, for example, is performed in cardiovascular, urological, gastrointestinal, neurovascular, and ophthalmic applications.

Catheters can allow drainage, administration of fluids or gases, access by surgical instruments, and perform wide variety of other tasks depending on the type of catheter. Catheters can, for instance, include energy emitting devices, such as laser and other radiation emitters, to ablate or cauterize tissue. In most uses, catheter is a thin, flexible tube ("soft" catheter) though catheters are available in varying levels of stiffness depending on the application.

Catheterization is normally performed in a series of steps. An introducer needle is first inserted into the body lumen followed by insertion of a guide wire through the introducer needle and into the lumen. The inserted introducer needle is removed, and an introducer sheath and/or dilator are introduced over the guide wire into the desired position to hold the body lumen open and allow insertion of tools, such as the catheter. The catheter can be introduced through the lumen of the introducer sheath using the wire as a guide.

In many applications, the rate of advancement and/or removal of catheters is important not only to patient safety but also to optimal usage of the catheter. Some catheters require a narrow range of advancement rates for effective performance. Laser catheters, for example, should be advanced at a rate of less than about 1 mm/second. Advancing too quickly can increase risk of injury (such as during superior vena cava during lead extraction), increase the forces acting at the laser sheath tip, and prevent the laser from properly ablating tissue (particularly with a smaller body lumen diameter with rapid catheter advancement). Advancing too slowly and lasing tissue too long can also provide poor results.

SUMMARY

These and other needs are addressed by the various aspects, embodiments, and configurations of the present disclosure. The disclosure is directed generally to an endovascular device monitoring system.

A method, according to this disclosure, can include the step of determining, by a microprocessor executable controller and based on movement of the endovascular device past a selected reference location, one or more of a movement rate of an endovascular device and position of a distal end of an endovascular device in a body of a patient.

A non-transient, tangible computer readable medium or system, according to this disclosure, can include microprocessor executable controller logic that, when executed, determines, based on endovascular device movement past a selected reference location, endovascular device movement rate and/or endovascular device distal end or tip position.

The rate is commonly one or more of velocity and acceleration of an endovascular device component.

The controller can detect, by an endovascular device movement sensor positioned at the selected reference location, displacement of one or more markers associated with the endovascular device.

Endovascular device movement can be determined by any of a number of techniques. Endovascular device movement, for example, can be based on one or more of rotation and displacement of a component mechanically engaged with a portion of the endovascular device; a variation in optical property of light reflected by the markers moving past the selected reference location (the variation being caused by the markers having an optical property different from that of other (intervening) parts of the endovascular device); a variation in magnetic field strength along a length of the endovascular device body (the variation being caused by the markers having a magnetic property different from that of other (intervening) parts of the endovascular device); and reading a radio frequency parameter associated with the markers (which can be an active and/or passive Radio Frequency-Identification ("RFID") tag).

The endovascular device movement sensor can be positioned on or adjacent to an introducer sheath assembly and/or the endovascular device itself.

The endovascular device movement sensor can be positioned externally or internally to the body of a patient.

When the controller determines that the endovascular device movement rate and/or distal end or tip position is unacceptable, the controller can, via a user interface, notify a user of the unacceptable movement rate and/or distal end or tip position in the body of the patient. Alternatively or additionally, the controller can cause a microprocessor executable endovascular device parameter adjustment module to adjust an endovascular device parameter. The endovascular device parameter can, for instance, be one or more of endovascular device velocity, endovascular device acceleration, endovascular device speed, endovascular device operational state, endovascular device position, and endovascular device energy emission level and/or intensity.

The present disclosure can provide a number of advantages depending on the particular configuration. The endovascular device monitoring system can not only detect and provide feedback to the user, such as whether endovascular device movement is too fast, too slow or just right, but also regulate endovascular device movement, thereby enabling physicians to gauge properly endovascular device movement during a procedure and providing optimal usage of the endovascular device (even for endovascular devices requiring a narrow range of advancement rates for effective performance). The movement of laser catheters, in particular, can be reliably, consistently, and accurately maintained at a rate of less than about 1 mm/second, providing a decreased risk of injury (particularly during superior vena cava during lead extraction), decreasing the forces acting at the laser sheath tip, and preventing the laser from improperly ablating tissue (particularly with a smaller body lumen diameter with rapid catheter advancement). The endovascular device monitoring system can also determine endovascular device distal end or tip position within the patient. This may operate in lieu of or complement an imaging system using radiopaque markers on the endovascular device to track endovascular device distal tip position.

These and other advantages will be apparent from the disclosure of the aspects, embodiments, and configurations contained herein.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_0$), It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "automatic" and variations thereof, as used herein, refers to any process or operation done without material human input when the process or operation is performed.

However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

A "catheter" is a tube that can be inserted into a body cavity, duct, lumen, or vessel. In most uses, a catheter is a thin, flexible tube ("soft" catheter), though in some uses, it is a larger, solid ("hard") catheter.

The term "computer-readable medium" as used herein refers to any storage and/or transmission medium that participate in providing instructions to a processor for execution. Such a medium is commonly tangible and non-transient and can take many forms, including but not limited to, non-volatile media, volatile media, and transmission media and includes without limitation random access memory ("RAM"), read only memory ("ROM"), and the like. Non-volatile media includes, for example, NVRAM, or magnetic or optical disks. Volatile media includes dynamic memory, such as main memory. Common forms of computer-readable media include, for example, a floppy disk (including without limitation a Bernoulli cartridge, ZIP drive, and JAZ drive), a flexible disk, hard disk, magnetic tape or cassettes, or any other magnetic medium, magneto-optical medium, a digital video disk (such as CD-ROM), any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. Computer-readable storage medium commonly excludes transient storage media, particularly electrical, magnetic, electromagnetic, optical, magneto-optical signals.

"Coronary catheterization" is a generally minimally invasive procedure to access the coronary circulation and/or blood filled chambers of the heart using a catheter. It is performed for both diagnostic and interventional (treatment) purposes.

The terms "determine", "calculate" and "compute," and variations thereof, as used herein, are used interchangeably and include any type of methodology, process, mathematical operation or technique.

A "lead" is a conductive structure, typically an electrically insulated coiled wire. The electrically conductive material can be any conductive material, with metals and intermetallic alloys common. The outer sheath of insulative material is biocompatible and biostable (e.g., non-dissolving in the body) and generally includes organic materials such as polyurethane and polyimide. Lead types include, by way of non-limiting example, epicardial and endocardial leads. Leads are commonly implanted into a body percutaneously or surgically.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The term "module" as used herein refers to any known or later developed hardware, software, firmware, artificial intelligence, fuzzy logic, or combination of hardware and software that is capable of performing the functionality associated with that element. Also, while the disclosure is presented in terms of exemplary embodiments, it should be appreciated that individual aspects of the disclosure can be separately claimed.

A "non-Newtonian fluid" is a fluid whose flow properties differ in any way from those of Newtonian fluids. Most commonly the viscosity (measure of a fluid's ability to resist gradual deformation by shear or tensile stresses) of non-Newtonian fluids is dependent on shear rate or shear rate history. However, there are some non-Newtonian fluids with shear-independent viscosity, that nonetheless exhibit normal stress-differences or other non-Newtonian behavior. Many salt solutions, suspensions, and molten polymers are non-Newtonian fluids. In a Newtonian fluid, the relation between the shear stress and the shear rate is linear, passing through the origin, the constant of proportionality being the coefficient of viscosity. In a non-Newtonian fluid, the relation between the shear stress and the shear rate is different and can even be time-dependent.

"Radio-Frequency Identification" (RFID) refers to the use of a wireless non-contact system that uses radio-frequency electromagnetic fields to transfer data from a tag attached to an object, for the purposes of automatic identification and/or tracking. Some tags require no battery and are powered and read at short ranges via magnetic fields (electromagnetic induction) (known as passive RFID tags). Others use a local power source and emit radio waves (electromagnetic radiation at radio frequencies) (known as active RFID tags). The tag contains electronically stored information which may be read from up to several meters away. Unlike a bar code, the tag does not need to be within line of sight of the reader and may be embedded in the tracked object.

A "surgical implant" is a medical device manufactured to replace a missing biological structure, support, stimulate, or treat a damaged biological structure, or enhance, stimulate, or treat an existing biological structure. Medical implants are man-made devices, in contrast to a transplant, which is a transplanted biomedical tissue. In some cases, implants contain electronics, including, without limitation, artificial pacemaker, defibrillator, electrodes, and cochlear implants. Some implants are bioactive, including, without limitation, subcutaneous drug delivery devices in the form of implantable pills or drug-eluting stents.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Endovascular device movement is monitored and/or controlled by an endovascular device monitoring system. The endovascular device monitoring system is commonly automated to avoid human error. While the endovascular device monitoring system is discussed with specific reference to catheters, it is to be understood that it can apply equally to other endovascular devices, such as lead removal or extraction sheaths, needles, surgical instruments, snares, and the like. The endovascular device monitoring system can be used for any type of catheter, including without limitation laser ablation, cauterization, and lead removal catheter systems.

Figure 1:
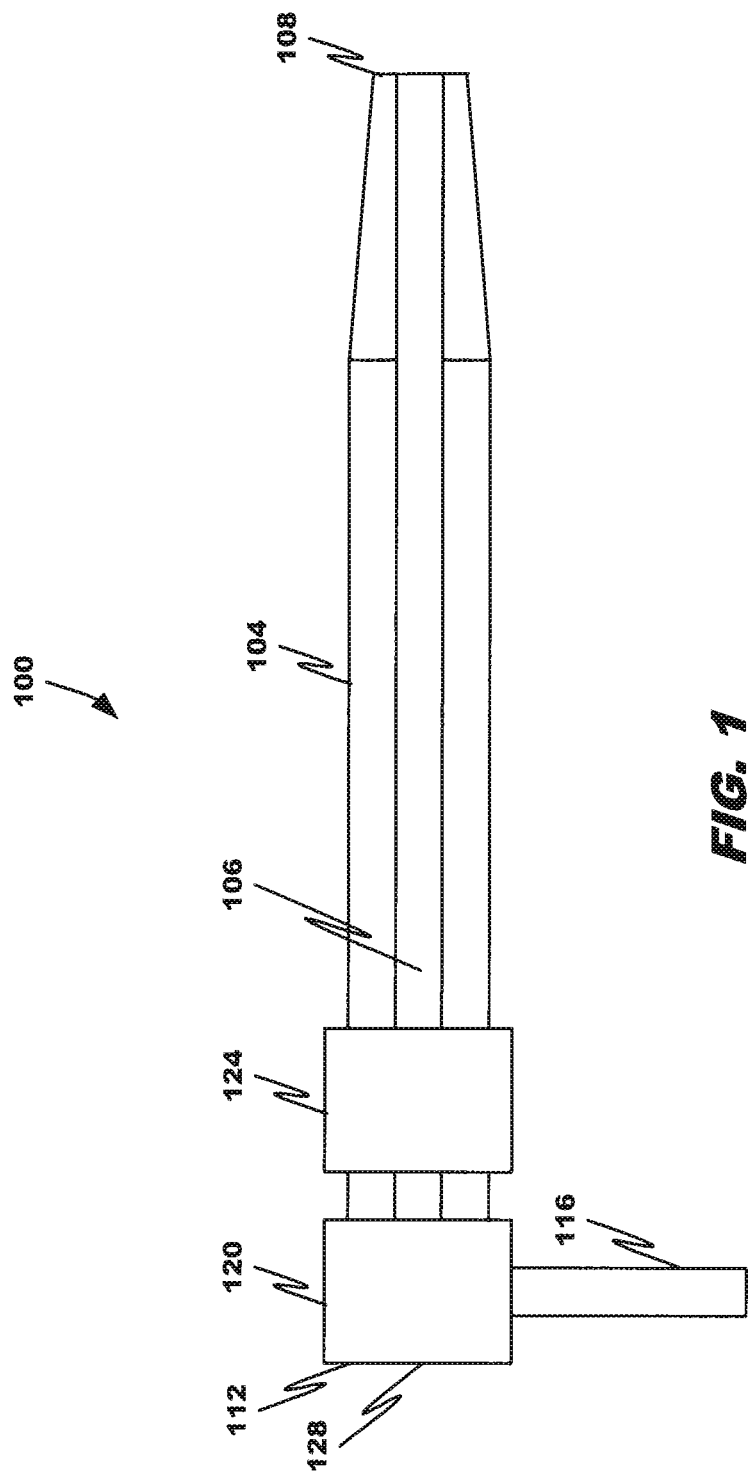
FIG. 1 depicts an introducer sheath assembly according to an embodiment of this disclosure.

FIG. 1 depicts an introducer sheath assembly 100 for monitoring catheter usage according to an embodiment. The introducer sheath assembly 100 includes a sheath 104 having a sheath lumen 106, a distal tip 108, and proximal end 112. The proximal end 112 includes a side port 116 in fluid communication with a valve 120 and a catheter movement sensor 124. A catheter (not shown) can be introduced through a main port 128 in the valve 120 or side port 116. The main port is coaxial with the sheath lumen 106.

Figure 5:
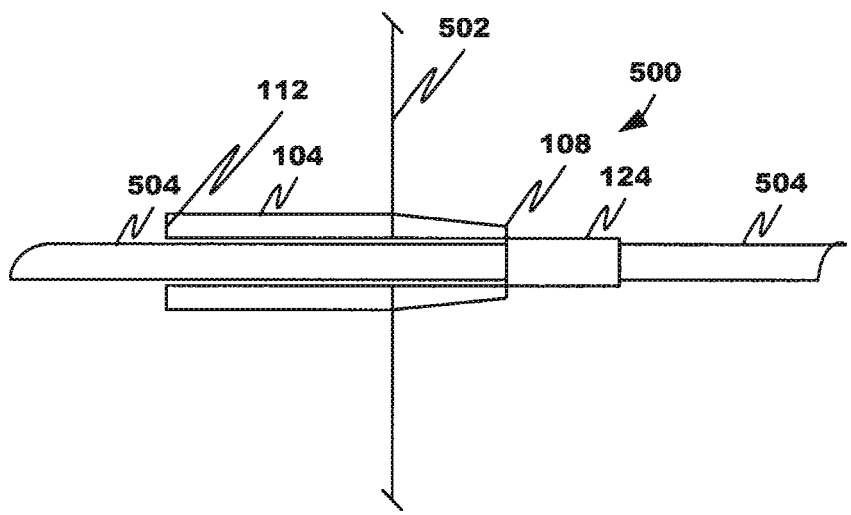
FIG. 5 depicts a catheter assembly according to an embodiment of this disclosure.

FIG. 5 depicts a catheter assembly 500 for monitoring catheter usage according to another embodiment. The catheter assembly 500 is positioned subcutaneously (underneath the skin 502 of a patient) and includes a catheter body 504 and a catheter movement sensor 124. The catheter movement sensor 124 is an integral part of the subcutaneous portion of the introducer sheath assembly.

Figure 6:
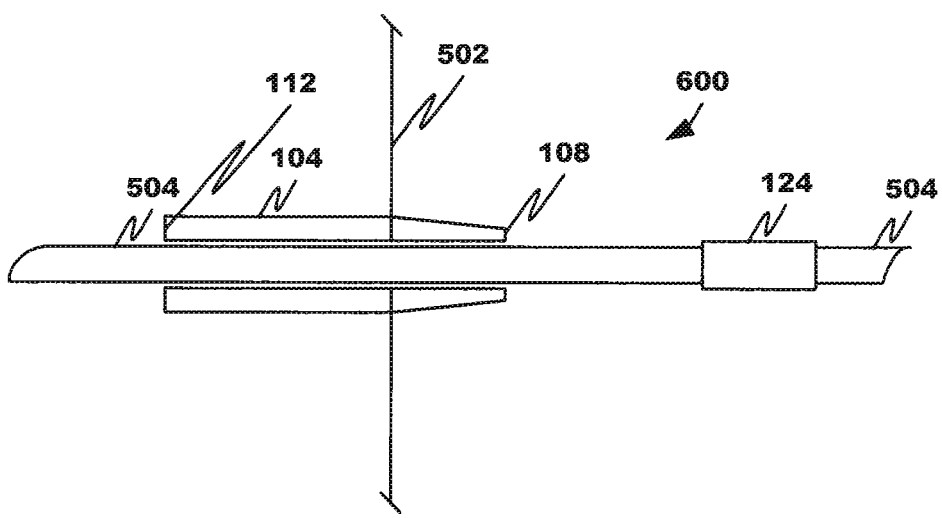
FIG. 6 depicts a catheter assembly according to an embodiment of this disclosure.

FIG. 6 depicts a catheter assembly 600 for monitoring catheter usage according to yet another embodiment. The catheter assembly 600 is positioned subcutaneously and includes a catheter body 504 and a catheter movement sensor 124. Unlike the catheter assembly 500, the catheter movement sensor 124 is an integral part of the catheter assembly. The catheter assembly 600 can be a modified version of a coronary laser atherectomy catheter by the Spectranetics Corporation under the tradenames ELCA™ and Turbo Elite™ (each of which is used for coronary intervention or catheterization such as recanalizing occluded arteries, changing lesion morphology, and facilitating stent placement) or a laser sheath sold under the tradename SLSII™ and GlideLight™ (which is used for surgically implanted lead removal).

The catheter movement sensor 124 in any of the above embodiments can have many different configurations. Velocity, speed, acceleration, and/or position of a catheter can be determined by one or more of mechanical, optical, ultrasound (acoustic), magnetic, electrical, and electromagnetic sensing techniques.

Figure 7:
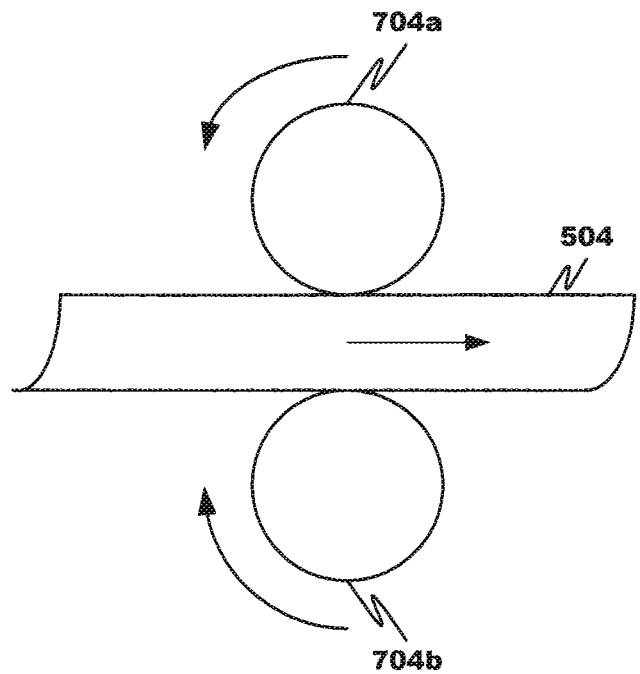
FIG. 7 depicts a catheter movement sensor according to an embodiment.

FIG. 7 illustrates an example of a mechanical sensing technique. The mechanical movement sensor 700 includes counter-rotating first and second wheels 704a,b engaging a catheter body 504 as it advances or withdraws from a body lumen. As will be appreciated, the velocity or rate of movement and position of the catheter body 504 are a function of the rate of rotation of the counter-rotating first and/or second wheel 704a,b. While position may be tracked using only one wheel engaging the catheter body 504, the frictional forces opposing catheter movement could be higher, thereby creating hindering catheter operation by the physician. Other mechanical techniques will be obvious to those of ordinary skill in the art.

Figure 8:
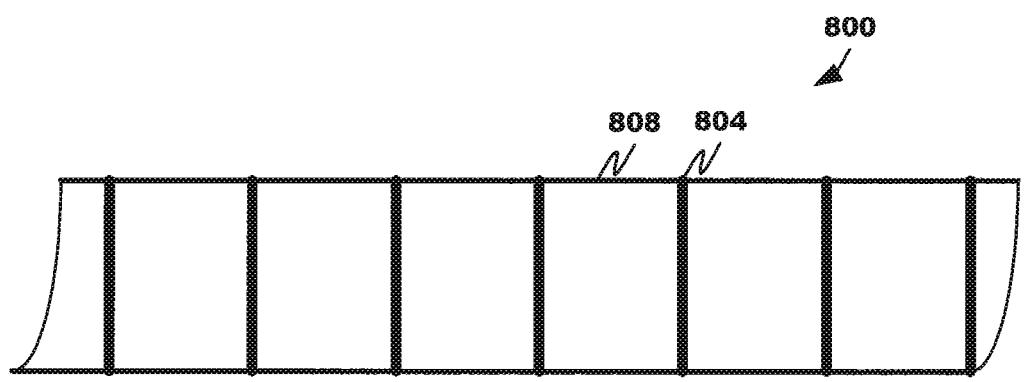
FIG. 8 depicts a catheter movement sensor according to an embodiment.

FIG. 8 illustrates an example of a radiation sensing technique in which the catheter movement sensor 124 includes not only a detector but also one or more markers 804 spaced at predetermined intervals 808 (which may be equidistant or non-equidistant) along a length of the catheter body 800. Adjacent markers may be used to start and stop a timer to measure a predetermined time interval required to transgress the intervening predetermined interval 808 and counting the transgressed markers to determine a subcutaneous length or approximate position of the distal tip of the catheter. The markers may be substantially identical or configured differently. An example of the latter is where each marker is detectably encoded (e.g., each marker being configured as a unique or substantially unique bar code) to represent a distance from a selected reference point.

The detector and markers of the catheter movement sensor 124 are typically located on different ones of the introducer sheath assembly 100 and catheter itself. For example, the markers can be located on the catheter body 800 as shown, and the detector on the introducer sheath assembly 100. Alternatively, the marker(s) can be located on the introducer sheath assembly 100, and the detector on or in the catheter.

In the case of optical sensing, the markers 804 can be any marker that reflects light in a detectable and consistent manner. The markers 804 typically have an optical property, such as reflectance (or reflectivity), absorbance (or absorption), and the like, different from that of the intervening catheter body 800. A light source emits modulated or unmodulated light onto the catheter body 800 as the catheter body 800 moves. Light reflected along a length of the catheter body 800 is captured by the detector typically configured as an array of photoelectric devices. The detector dissects the reflected light into its various spectra. The differing optical properties of the light reflected by the markers when compared with the intervening catheter body 800 are translated into an electric signal, which is output to a controller.

In the case of magnetic sensing, the markers are magnetic or have a magnetic property different from that of the intervening catheter body 800. The detector can be a magnetic field sensor, such as a rotating coil, Hall effect magnetometer, NMR magnetometer, SQUID magnetometer, or fluxgate magnetometer that can measure variations in magnetic field strength along a length of the catheter body 800 and thereby locate the markers. The measured magnetic field variations when compared with the intervening catheter body 800 are translated into an electric signal, which is output to a controller.

In the case of ultrasonic sensing, the markers have a different ultrasonic transmission property than the intervening catheter body 800. An ultrasound transducer can act both as the ultrasonic emitter and detector to detect reflected or transmitted ultrasonic energy and thereby locate the markers. An electrical signal is generated when each marker passes the detector, which signal is output to a controller.

In the case of sensing using other wavelengths of radiation (such as x-rays), the markers can include a radiopaque material, such as gold or other metal, while the intervening catheter body 800 includes a radiolucent material, or vice versa, such that the markers have a different imaging property than the intervening catheter body 800. An electrical signal is generated when each marker passes a conventional detector, which signal is output to a controller.

In the case of electrical sensing, the markers are electrically conductive or have an electrical conductivity or resistivity different from that of the intervening catheter body 800. An electrical parameter, such as voltage, current, resistance, or ambient electric field can be detected to determine marker location. The detector, for example, can be a voltmeter, ammeter, magneto resistive field sensor, Hall Effect current sensor transducer, potentiometer, oscilloscope, LCR meter, and the like. An electrical signal is generated when each marker passes the detector, which signal is output to a controller.

An example of sensing using a combination of electromagnetic energy and electrical sensing is radio-frequency identification. The markers can be configured as active or passive RFID tags. In one configuration, the markers are configured as passive RFID tags, and the detector as an active or powered RFID reader. In another configuration, the markers are configured as active RFID tags, and the detector as an active or passive RFID reader.

As will be appreciated, the above discussion presents examples only and is not intended to be exhaustive. One of ordinary skill in the art will appreciate that other sensing techniques can be employed depending on the application.

Figure 2:
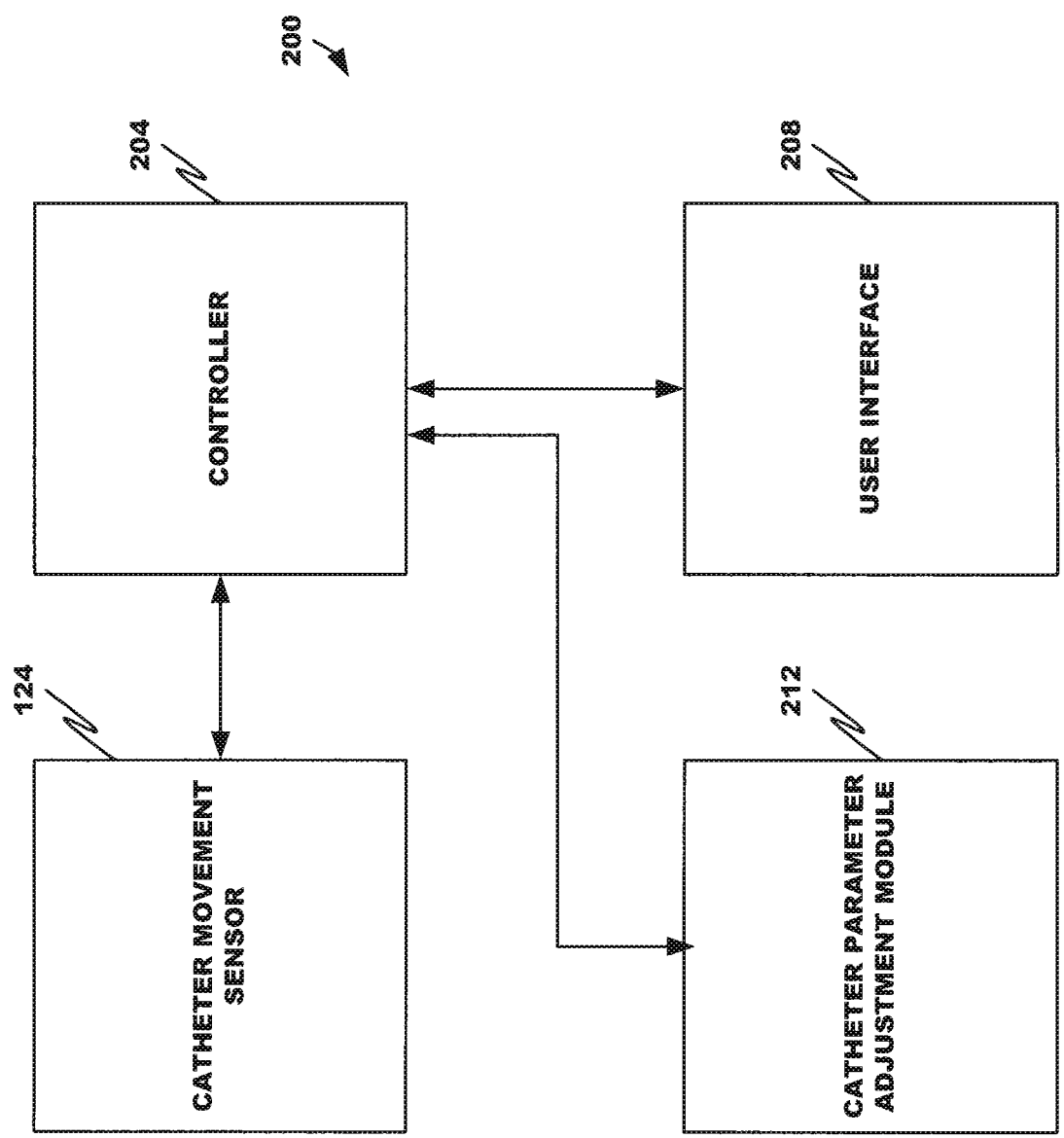
FIG. 2 depicts a catheter monitoring system according to an embodiment of this disclosure.

FIG. 2 depicts a catheter monitoring system 200 according to an embodiment. The catheter monitoring system 200 includes the catheter movement sensor 124 in signal communication with a controller 204, which is, in turn, in signal communication with a user interface 208 and a catheter parameter adjustment module 212. The controller 204 executes one or more microprocessor executable control algorithms stored in a computer readable medium to receive catheter movement signals from the catheter movement sensor 124 and, based on the received catheter movement signals, provide alarm and other output to the user via user interface 208 and/or effect catheter parameter adjustment via the catheter parameter adjustment module 212. The user interface can provide audible (e.g., sounds), tactile, and/or visual (e.g., lights) output to the user and receive user commands as input to the controller 204. Audible, tactile, and/or visual output relates to one or more of catheter movement and/or catheter distal tip location within the body lumen. The catheter parameter(s) adjusted by the catheter parameter adjustment module 212 include one or more of catheter velocity, acceleration, speed, operational state (e.g., on or off), catheter energy emission level or intensity, catheter (distal end) position, and the like.

Catheter parameter adjustment or regulation can be affected by various techniques. Catheter velocity, acceleration, and/or speed can be adjusted by selectively and/or variably increasing resistance to catheter movement, such as by hydraulic resistance applied to the catheter or a part thereof, frictional resistance applied to the catheter or a part thereof by a braking system, resistance posed by movement of the catheter or a part thereof through a non-Newtonian fluid (such as Dilitant), resistance created by movement of a magnetic material associated with the catheter through an external magnetic field (which may be from a magnet or flow of charged particles), and other means of slowing or retarding catheter movement. Catheter operational state can be controlled or regulated by turning an energy emitter in the catheter on or off, catheter energy emission level or intensity can be controlled or regulated by altering a degree of energization of a power source of the energy emitter.

Figure 3:
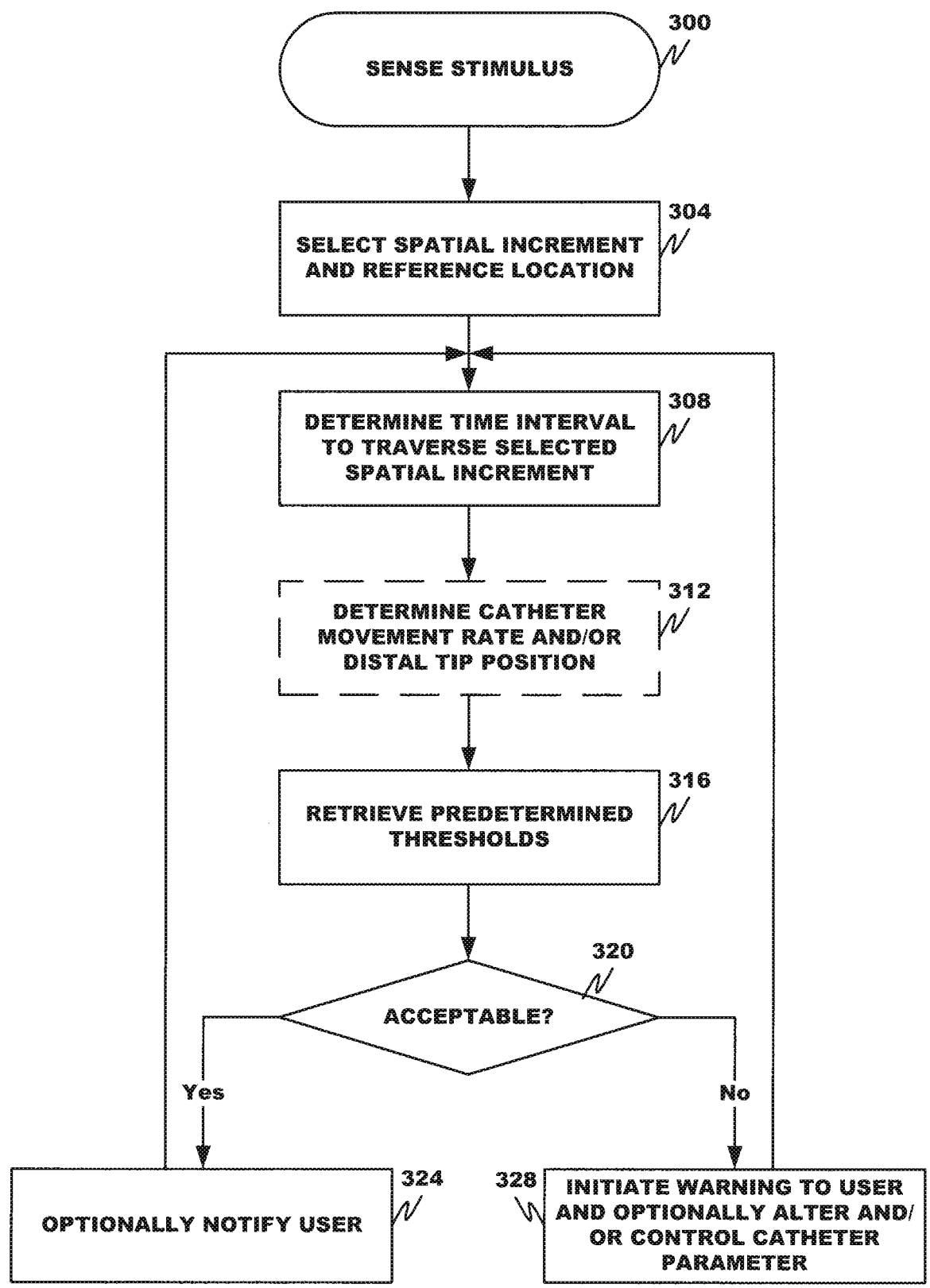
FIG. 3 depicts a control algorithm according to an embodiment of this disclosure.

An operation of the controller 204 will now be described with reference to FIG. 3.

Operation commences when the controller 204 senses a stimulus in step 300. The stimulus, for example, can be receipt of user input, receipt of a catheter movement signal from the catheter movement sensor 124, passage of time, and the like.

In step 304, the controller 204 selects a spatial increment over which to determine catheter velocity, acceleration, and/or speed and, if necessary, a reference location at which to detect, track or otherwise observe marker movement. A typical selected spatial increment is the spatial interval between adjacent markers 804, though the selected spatial increment can span more than two increments depending on the application. Differently sized spatial intervals can be selected for different types of procedures and/or catheters. Typically, the reference location is the location of the catheter movement sensor 124 or a component thereof.

In step 308, the controller 204 determines the time interval required for the catheter to traverse the selected spatial increment. The time interval can be determined, for example, by initiating or reading a start time on a timer (not shown) when a first marker passes a detector and terminating or reading a stop time on the timer when the marker associated with the end of the selected spatial increment passes the detector.

In optional step 312, the controller 204 determines a catheter movement rate (e.g., velocity, acceleration, and/or speed) and/or distal tip position (based on the number of markers that have transgressed the detector). Depending on the application, this step may be unnecessary where the time interval is mapped directly to a lookup table showing acceptable and unacceptable time intervals and/or the number of transgressed markers is mapped directly to the subcutaneous length of the catheter and therefore the approximate catheter distal tip position.

In step 316, the controller 204 retrieves predetermined catheter movement and/or catheter distal tip position thresholds. The predetermined thresholds can have a corresponding rule regarding a response if the predetermined threshold is triggered. The rule, for example, can be to provide audible, tactile, and/or visual output to the user, alter a catheter parameter, and/or regulate a catheter movement rate.

In decision diamond 320, the controller 204 determines, based on a comparison of a predetermined threshold to the determined catheter movement rate and/or determined time interval and/or catheter distal tip position, whether catheter movement and/or position is/are acceptable. When acceptable, the controller 204 proceeds to step 324 and optionally notifies the user accordingly. When unacceptable, the controller 204 proceeds to step 328 and initiates a warning to the user and/or alters/controls one or more catheter parameters as described previously. After completing steps 324 and 328, the controller 204 returns to and repeats step 308.

Figure 4:
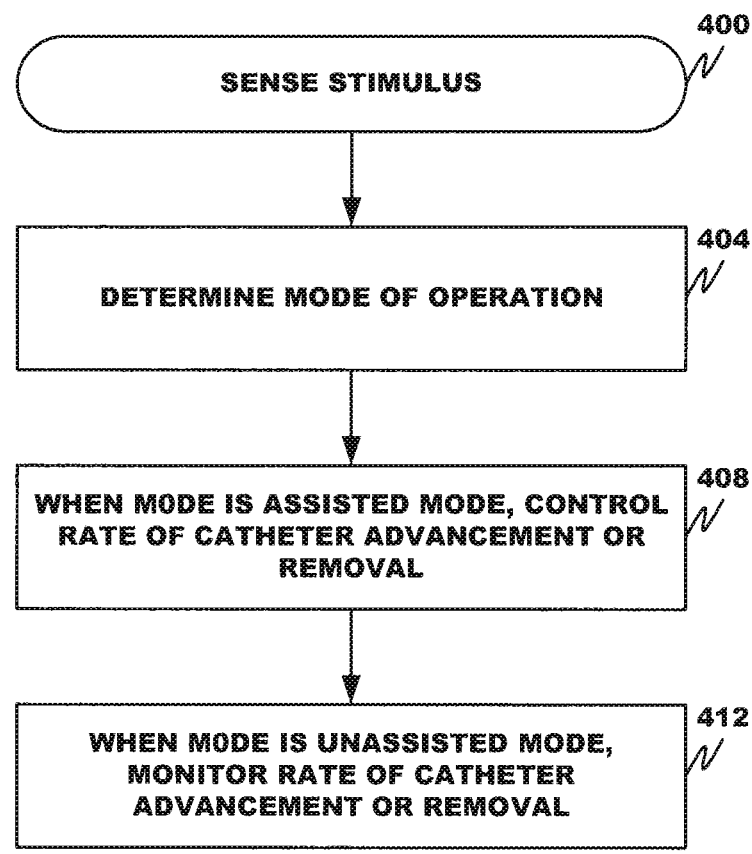
FIG. 4 depicts a control algorithm according to an embodiment of this disclosure.

A further operation of the controller 204 will now be described with reference to FIG. 4. The operation is based on user selection between an assisted and unassisted mode of operation. The assisted mode of operation enables the controller not only to provide audible, tactile, and/or visual feedback to the user but also regulate one or more catheter parameters. The unassisted mode of operation enables the controller to provide audible, tactile, and/or visual feedback to the user but not to regulate one or more catheter parameters.

In step 400, the controller 204 senses a stimulus, including those indicated above.

In step 404, the controller 204 determines a current mode of operation. The current mode of operation is typically selected by the user but can default to an assisted mode when catheter operation is unacceptable.

In step 408, the controller 204 determines that the current operating mode is the assisted mode and, in response, controls a rate of catheter advancement or removal using any of the techniques noted above.

In step 412, the controller 204 determines that the current operating mode is the unassisted mode and, in response, monitors the rate of catheter advancement or removal and provides appropriate audible, tactile, and/or visual output to the user.

A number of variations and modifications of the disclosure can be used. It would be possible to provide for some features of the disclosure without providing others.

For example, in one alternative embodiment, the teachings of this disclosure are used with an unpowered catheter mounting any one or more of a variety of tools, such as dilation balloons, cutting balloons, cutting blades, drug release mechanisms, imaging devices, blood flow sensors, contrast media, and the like.

The present disclosure, in various aspects, embodiments, and configurations, includes components, methods, processes, systems and/or apparatus substantially as depicted and described herein, including various aspects, embodiments, configurations, sub combinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included the description of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system comprising:
   a sheath;
   a laser catheter configured to receive laser energy, the laser catheter configured to move relative to the sheath, wherein the laser catheter comprises a distal tip, and wherein the sheath or the laser catheter comprises a sensor configured to sense a position of the distal tip of the laser catheter; and
   a controller comprising a non-transient, tangible computer readable medium including logic, whereupon execution of the logic, the controller is configured to:
   monitor an output of the sensor to determine a rate of manual advancement or removal of the laser catheter by an operator of the laser catheter;
   compare the determined rate of with at least one threshold movement rate;
   when the determined rate of movement falls outside the at least one threshold rate of movement, controlling
   receive a selection signal configured to place the controller in an assisted mode or an unassisted mode;
   (A) when the selection signal places the controller in the assisted mode, the controller is configured to monitor an output of the sensor to determine a manual and unregulated rate of advancement or removal of the laser catheter by an operator of the laser catheter, and in response to a determination that the manual and unregulated rate of advancement or removal falls outside a threshold range, to automatically regulate the rate of advancement or removal of the laser catheter; and
   (B) when the selection signal places the controller in the unassisted mode, the controller is configured to monitor an output of the sensor to determine a manual and unregulated rate of advancement or removal of the laser catheter by an operator of the laser catheter, and in response to a determination that the manual rate of advancement or removal falls outside a permissible threshold, to generate an operator alert without automatically regulating the rate of advancement or removal of the laser catheter.

2. The system of claim 1, wherein, in the assisted mode and not in the unassisted mode, the controller is further configured to automatically control an operational parameter of the laser catheter in response to the determination that the manual rate of advancement or removal falls outside a permissible threshold.

3. The system of claim 2, wherein the operational parameter is an emission of the laser energy by the laser catheter.

4. The system of claim 2, wherein the operational parameter is an intensity of the laser energy emitted by the laser catheter.

5. The system of claim 1, wherein the operator alert comprises at least one of audible, tactile and visual feedback to the operator.

6. The system of claim 5, wherein the feedback comprises audible feedback.

7. The system of claim 6, wherein the feedback further comprises tactile or visual feedback.

8. The system of claim 6, wherein the feedback further comprises tactile feedback.

9. The system of claim 5, wherein the feedback comprises tactile feedback.

10. The system of claim 9, wherein the feedback further comprises audible or visual feedback.

11. The system of claim 5, wherein the feedback comprises visual feedback.

12. The system of claim 1, wherein the rate of advancement or removal is a velocity of the laser catheter.

13. The system of claim 1, wherein the rate of advancement or removal is an acceleration of the laser catheter.

14. The system of claim 1, wherein the controller receives a signal indicative of a position of the distal tip from the sensor.

15. The system of claim 14, wherein the sensor is configured to sense the position of the distal tip of the laser catheter relative to the sheath.

16. The system of claim 15, wherein the controller is configured to determine a rate of advancement or removal of the laser catheter based on the sensed position of the distal tip of the laser catheter relative to the sheath the signal indicative of the position of the distal tip.

17. A system comprising:
   a sheath;
   a laser catheter configured to receive laser energy, the laser catheter configured to move relative to the sheath, wherein the laser catheter comprises a distal tip, and wherein the sheath or the laser catheter comprises a sensor configured to sense a position of the distal tip of the laser catheter; and
   a controller comprising a non-transient, tangible computer readable medium including logic, whereupon execution of the logic, the controller is configured to:
   when the selection signal places the controller in an assisted mode, selectively regulate an operational parameter of the laser catheter;
   when the selection signal places the controller in an unassisted mode, provide feedback to a user and not regulate the one or more operational parameters; and
   switch between the assisted mode and the unassisted mode based on a user selection between the assisted and unassisted modes; and
   wherein, the assisted mode, the operational parameter is transitioned automatically from unregulated to regulated when an unacceptable catheter operation is detected by the controller while the operational parameter is unregulated, the unacceptable catheter operation comprising an unacceptable movement rate of the distal tip based on a comparison of a predetermined threshold to the determined laser catheter movement rate and/or distal tip position.

18. The system of claim 17, wherein the unacceptable catheter operation is an unacceptable rate of advancement or removal of the laser catheter.

19. The system of claim 18, wherein the operational parameter is the rate of advancement or removal of the laser catheter.

20. The system of claim 18, wherein the operational parameter is an emission of the laser energy by the laser catheter or an intensity of the laser energy emitted by the laser catheter.

* * * * *